United States Patent [19]

Salce et al.

[11] Patent Number: 4,950,445

[45] Date of Patent: Aug. 21, 1990

[54] METHOD OF VACUUM FORMING DISPOSABLE FACESHIELD

[75] Inventors: Arthur J. Salce; Richard T. Metcalfe, both of Southbridge, Mass.

[73] Assignee: Cabot Safety Corporation, Southbridge, Mass.

[21] Appl. No.: 206,597

[22] Filed: Jun. 14, 1988

Related U.S. Application Data

[63] Continuation-in-part of Ser. No. 152,624, Feb. 5, 1988, abandoned.

[51] Int. Cl.⁵ ............................................. B29C 51/10
[52] U.S. Cl. .................................. 264/549; 264/2.7; 264/553; 425/388
[58] Field of Search ............... 264/553, 544, 547, 548, 264/549, 554, 571, 1.1, 2.7, 550; 425/388, 816

[56] References Cited

U.S. PATENT DOCUMENTS

| 2,367,642 | 1/1945 | Helwig | 264/544 |
| 2,440,499 | 4/1948 | Ames et al. | 264/544 |
| 3,971,687 | 7/1976 | Greer et al. | 264/553 |
| 4,352,776 | 10/1982 | Weisner et al. | 264/2.7 |

FOREIGN PATENT DOCUMENTS

| 79/00062 | 2/1979 | PCT Int'l Appl. | 264/553 |
| 1103563 | 2/1968 | United Kingdom . | |

Primary Examiner—Jill L. Heitbrink
Attorney, Agent, or Firm—Fishman, Dionne & Cantor

[57] ABSTRACT

A method of making a protective shield with an optically clear viewing portion by vacuum forming over a mandrel wherein the viewing portion of said protective shield is maintained out of contact with the mandrel to define the optically clear viewing portion.

10 Claims, 9 Drawing Sheets

METHOD OF VACUUM FORMING DISPOSABLE FACESHIELD

CROSS-REFERENCE TO RELATED APPLICATION:

This is a continuation-in-part of U.S. application Ser. No. 152,624 filed Feb. 5, 1988 now abandoned.

BACKGROUND OF THE INVENTION

This invention relates to a one-piece, lightweight protective faceshield, particularly one having a viewing zone of maximum optical clarity, and a method of making such a faceshield.

Various types of faceshields are known in the art, many of which are designed to protect the wearer against flying projectiles. Such faceshields are generally comprised of multi-components, such as a clear viewing/shield portion affixed to a helmet or visor unit and are generally fabricated of relatively thick, impact-resistant plastic. There are generally known two preferred methods for fabricating a faceshield with acceptable optical clarity.

In one method, the faceshield may be injection molded in a mold that has a highly polished surface. Such processes generally require that the molded part have a thickness in excess of 0.040 inch (1.02 mm) to achieve reasonable polymer flow into the mold. Other than the thickness of the part, which is acceptable for most applications, this method produces very high quality precision parts of any desired configuration.

In a second method, a blank may be taken from an optically polished flat polymer sheet (the sheet is polished usually by pressing between two platens) and formed in a curved piece (i.e. cylindrical, not spherical) by heating the blank beyond its glass transition temperature and applying force in the direction of the desired curve. This method generally retains the optics of the original polished sheet, but is only suitable for simple curved pieces and cannot be utilized where the desired piece has a complex configuration.

It is now recognized that there is a need in the medical profession (the term "medical" as used herein is intended to encompass the medical, dental and related professions) for a lightweight, preferably disposable, faceshield to protect the medical professional from splattered body fluids so as to avoid the possibility of contamination therefrom. While certainly many of the heretofore known goggles and faceshields might serve this purpose, such products tend to be bulkier and heavier than is desired by the medical professional and are far too costly to be considered disposable.

SUMMARY OF THE INVENTION

The above-discussed and other problems and deficiencies of the prior art are overcome or alleviated by the inexpensive one-piece, lightweight protective faceshield of the present invention which is particularly well suited for use in the medical profession.

The present invention comprises a one-piece, lightweight protective faceshield comprising a curved brow member adapted to substantially conform with and contact a wearer's forehead; a faceshield body extending outwardly and downwardly from said brow member and integral therewith, said faceshield body being adapted to cover at least a portion of the wearer's face without contacting any part thereof below the forehead; and means for retaining said brow member in contact with the wearer's forehead.

The present invention also comprises a one-piece, lightweight eye protective shield comprising an eye protective member adapted to shield a wearer's eyes from splattered liquid or soft foreign matter, said eye protective member being fabricated of a transparent thermoplastic film less than 0.030 inch (0.76 mm) thick and having an integral viewing portion disposed in the wearer's viewing path, wherein said viewing portion has retained the same or better optical clarity as the thermoplastic film from which said shield is fabricated.

In addition, the present invention comprises a method of making a protective shield with a viewing portion of maximum optical clarity which comprises vacuum forming a transparent thermoplastic film over a forming mandrel of the desired shape wherein said forming mandrel is designed such that said viewing portion of said protective shield does not contact any part thereof.

In a preferred embodiment, the one-piece, disposable faceshield is retained or secured onto the wearer's head by either a reusable or disposable headband. The reusable headband comprises a visor having a pair of opposed resilient arms for securing to the head. Suitable attaching means such as a series of studs or snap shaped protrusions are provided to the visor and faceshield for easily attaching and removing faceshields from the visor. The disposable headband comprises a semi circular piece terminating at a pair of opposed resilient arms. This disposable headband may be ultrasonically welded or otherwise attached to the faceshield. Alternatively, the disposable headband may be injection or otherwise molded to the previously vacuum formed one-piece faceshield.

The above discussed and other features and advantages of the present invention will be appreciated and understood by those of ordinary skill in the art from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENTS

Figure 1:
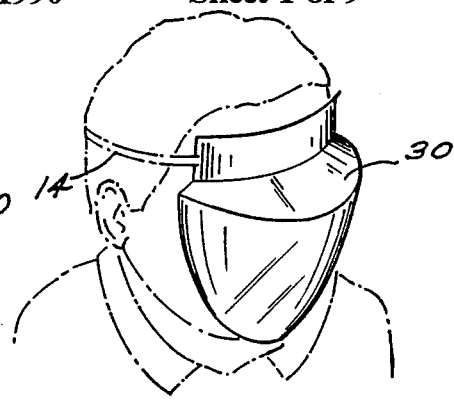
FIG. 1 illustrates a faceshield of the present invention as it would be worn by a wearer.

With reference to the drawings, the preferred faceshield of the present invention is illustrated in FIGS. 2-5. The faceshield 10 comprises a curved brow member 11 which is adapted to substantially conform with and contact a wearer's forehead, as shown in FIG. 1. The uppermost edge 12 of the curved brow member is advantageously curved away from the wearer's forehead to avoid contact of the forehead with any sharp edges which might cause discomfort. A faceshield body 13 (also referred to as eye protective shield) extends first outwardly at surface 30, then downwardly from the curved brow member and is integral therewith. The faceshield body is adapted to cover at least a portion of the wearer's face (i.e. at least the wearer's eyes) without contacting any part of the face below the forehead. When means for retaining the curved brow member against the wearer's forehead, such as elastic band 14, are affixed to the faceshield, the faceshield can be comfortably worn as shown in FIG. 1, with the curved brow member 11 providing a solid comfortable fit.

The above-described faceshield is advantageously fabricated as one-piece out of a transparent, optical grade, thermoplastic material. To keep the product lightweight and inexpensive, and optionally disposable, the faceshield should have a thickness of less than 0.030 inch (0.76 mm), preferably less than 0.020 inch (0.151 mm) and most preferably less than 0.015 inch (0.38 mm).

Looking at other features of the faceshield of the present invention, the faceshield body can be seen to comprise an upper viewing portion 15 which is disposed in the wearer's viewing path. This viewing portion is preferably bubble-shaped to preserve optical clarity as will be explained below. If the faceshield is designed to extend below the eyes, a lower portion 16 extends downwardly from the upper viewing portion. It has been found to be particularly advantageous to fabricate the lower portion 16 so that it first extends outwardly slightly from the upper viewing portion, then downwardly, as can be more clearly seen in FIG. 5, so as to create a deflecting point 17 to direct exhaled air away from the upper viewing portion.

Careful attention is required to achieve the maximum optical clarity in the viewing portion 15 since obviously any flaw or distortion in this area will detract from the usefulness and acceptance of the product. A new method of manufacturing the above-described faceshield has now been discovered which results in a viewing portion of maximum optical clarity.

As a result of this new method, it is possible to fabricate the faceshield in such a way that the viewing portion will retain the same optical clarity as the original thermoplastic film from which the faceshield is fabricated, and possibly even better optical clarity. That is, unlike other fabricating methods which can adversely affect the optics, the present method retains good optical properties. In fact, the viewing portion of the present faceshield has a minimum resolution of 20, preferably at least 24, determined on a National Bureau of Standards Resolution Test Chart, Special Publication 374 (ANSI Z87.1-1979, Sec. 6.3.4.1.3).

This is an extremely significant discovery since, because of the thinness of the present faceshield, it cannot be fabricated using injection molding techniques in which good optics can be preserved. The only economically feasible method for fabricating a thin piece like the present faceshield is to vacuum form a thermoplastic film over a mandrel shaped to the desired configuration. This is the typical method of making items such as yogurt containers and blister packs. The problem with this method, however, is that an undesirable amount of optical degradation or distortion occurs as the film contacts the mandrel surfaces. Thus, this method would not ordinarily be suitable for fabricating pieces requiring maximum optical clarity.

The method utilized in the present invention is essentially identical to currently known vacuum forming techniques with the exception that the forming mandrel has been modified in the area corresponding to the viewing portion of the faceshield. This modification will be described later. In the typical vacuum forming process a transparent thermoplastic film is taken from a roll or sheet, heated and allowed to conform to the shape of a three-dimensional forming tool or mandrel where, after cooling, it is removed from the mandrel and die cut from the sheet.

Figure 8:
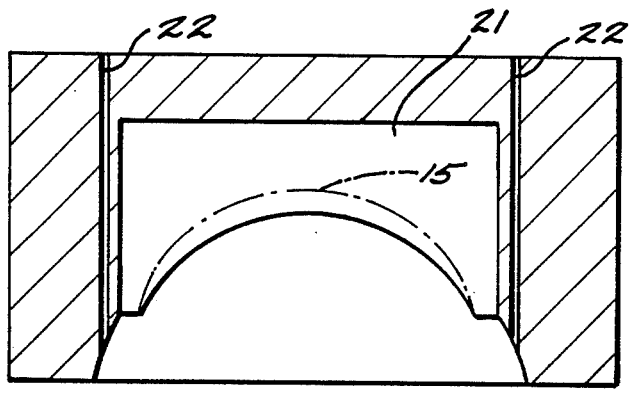
FIG. 8 is a sectional view of the forming mandrel illustrated in FIG. 6, taken along the line 8—8.
Figure 6:
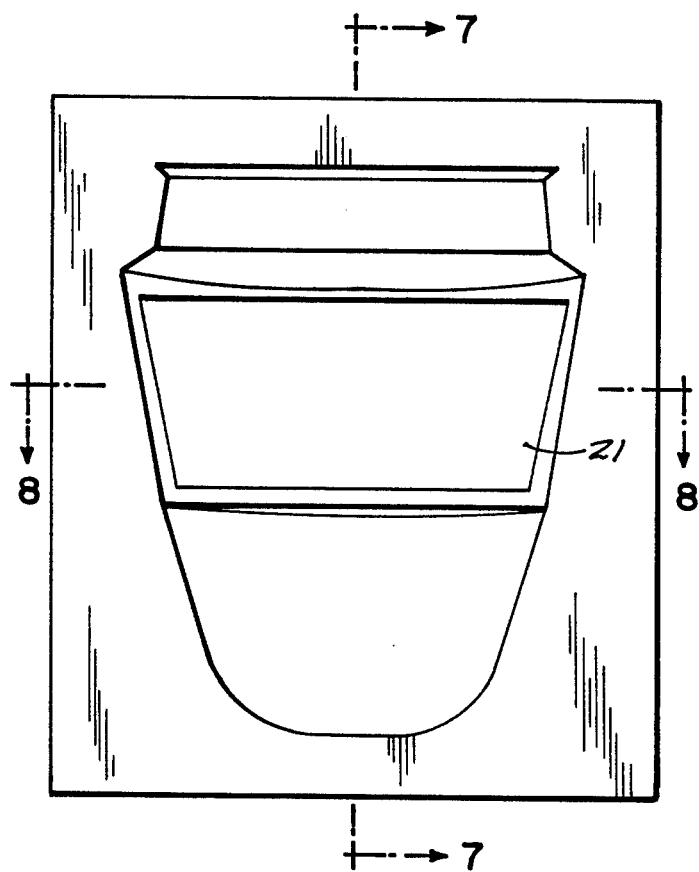
FIG. 6 is a top plan view of a forming mandrel on which the faceshield illustrated in FIG. 2 is formed.
Figure 7:
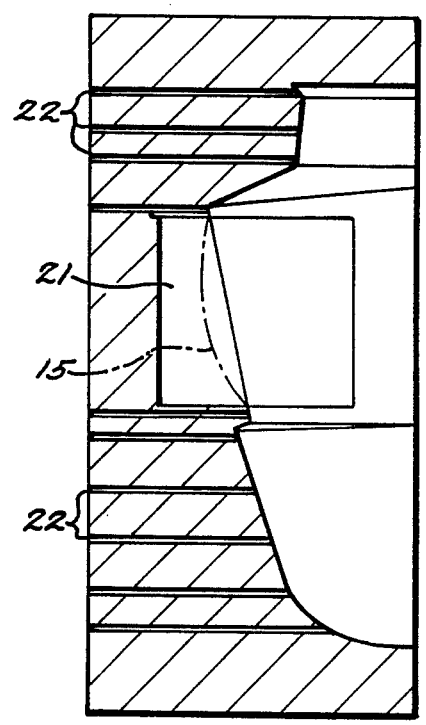
FIG. 7 is a sectional view of the forming mandrel illustrated in FIG. 6, taken along the line 7—7.
Figure 18:
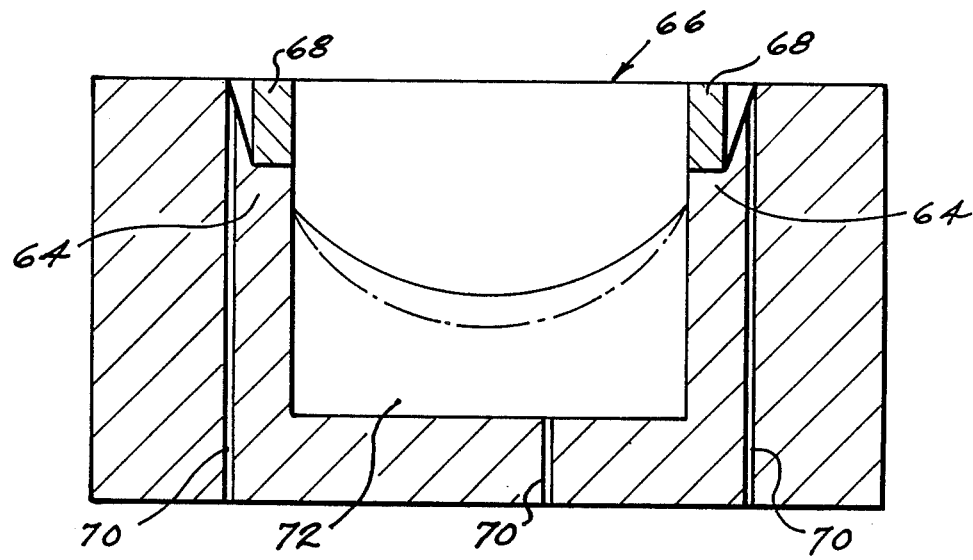
FIG. 18 is a schematic view of a mold used to form the faceshield of FIG. 10.

As shown in FIGS. 6-8, the forming mandrel 20, which is utilized to form the faceshields of the present invention, is a three-dimensional female mold made of polished cast aluminum which conforms in every respect to the desired shape of the faceshield. However, the mandrel cutaway portion (or pocket) 21, which corresponds to the viewing portion 15 of the faceshield, has been cut away so that during the forming process, the film which forms the viewing portion 15 of the faceshield, which is shown in phantom in FIGS. 7-8, sags into a bubble shape within the cutaway portion but does not contact any part of the mandrel. In this manner, the optical clarity of the original thermoplastic film is maintained, and in some cases is improved due to a stretching of the material as it sags into the cutaway portion. Vacuum holes 22 extend throughout the mandrel, except the cutaway portion, through which a vacuum can be applied to assist the conformation of the heated thermoplastic film to the mandrel surface. Optionally, a hole connecting the cutaway portion to the outside atmospheric pressure, or some other pressure source, can be employed to control the size of the bubble that forms the viewing portion as is shown in FIG. 18.

Figure 9:
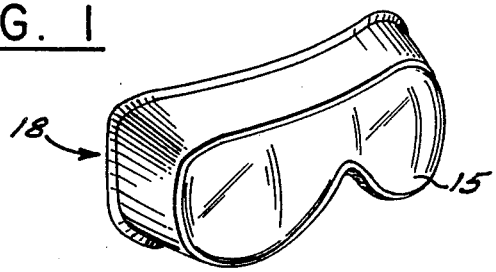
FIG. 9 is a perspective view of a goggle of the present invention having a bubble shaped viewing area.
Figure 3:
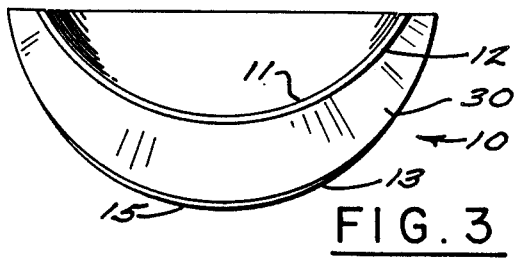
FIG. 3 is a top plan view of the faceshield illustrated in FIG. 2.
Figure 5:
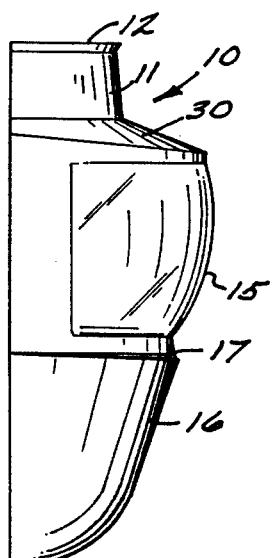
FIG. 5 is a side elevational view of the faceshield illustrated in FIG. 2.
Figure 4:
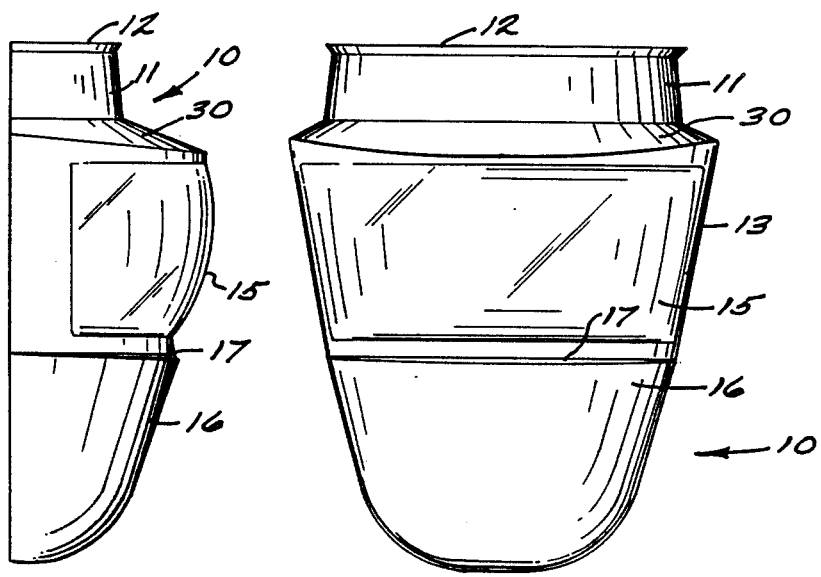
FIG. 4 is a front elevational view of the faceshield illustrated in FIG. 2.

In like manner, an eye protective shield in the form of a goggle 18, as shown in FIG. 9, can be fabricated utilizing the method of this invention. Such a goggle will have a bubble-shaped viewing portion 15 similar to the viewing portion of the faceshield described earlier.

As mentioned previously, the faceshield of the present invention may be fabricated out of any transparent, optical grade, thermoplastic film including films of polymeric resins selected from polycarbonates, polyesters, copolyesters, polyvinyl chloride, cellulose alkylates (including cellulose acetates, propionates and butyrates) polysulfones, polyether sulfones and polystyrenes. Preferred polymeric resins are polycarbonate of bisphenol-A, particularly G.E. graphic grade 8010 polycarbonate from General Electric, polyethylene terephthalate, and Kodar PETG Copolyester 6763 from Eastman Chemical Products. Such polymeric films should have a thickness in the range of about 0.005 to 0.030 inch (0.013 to 0.76 mm), most preferably 0.005 to 0.015 inch (0.013 to 0.38 mm).

A suitable manufacturing process for the faceshield of the present invention is as follows: A transparent thermoplastic film such as Kodar P.E.T.G. Copolyester 6763, manufactured by Eastman Chemical Products, Inc., of Kingsport, Tenn. is fed from a roll form approximately 24 inches wide into a conventional vacuum forming machine. This film may be treated with a denesting agent to allow easier release from the forming tools. The film may also have a protective coating on front or back sides, or inter-leaving material to protect the film surface. These protective coatings are stripped from the film before the film is heated. The film is advanced to a heating station where it is brought beyond its glass transition temperature, which in the case of P.E.T.G. 6763 is preferably about 320° F. The heated film begins to sag at this elevated temperature and is then brought into contact with the forming tools. The forming tools can be either male or female and may be multiple in number. In this case female forming tools made of polished cast aluminum, as shown in FIGS. 6–8, are employed. These forming tools are temperature controlled at about 150° F. A vacuum of approximately 25 inches of mercury is drawn through holes 22 on the interior of the forming tools which allows outside atmospheric pressure to force the film to comply to the forming tool shape. The pocket 21 where the optical viewing portion is located has had material removed from the forming mandrel so that the film forms a natural curved shape without touching the mandrel. There are no vacuum holes entering the pocket that forms the optical viewing area. The film is withdrawn from the female forming mandrels and indexed to the next position where the parts are die cut from the film web. At the die cutting station, the preformed parts are positioned in a matched set of male and female blanking tools where they are cut from the web. It can be arranged so that the part is held slightly in the web for indexing to the final station where they are broken free. Information may be stamped on the part as desired by engraving the forming mandrel with the desired information. After the part has been die cut from the roll, a headband is attached by stapling or other means of attachment.

Figure 10:
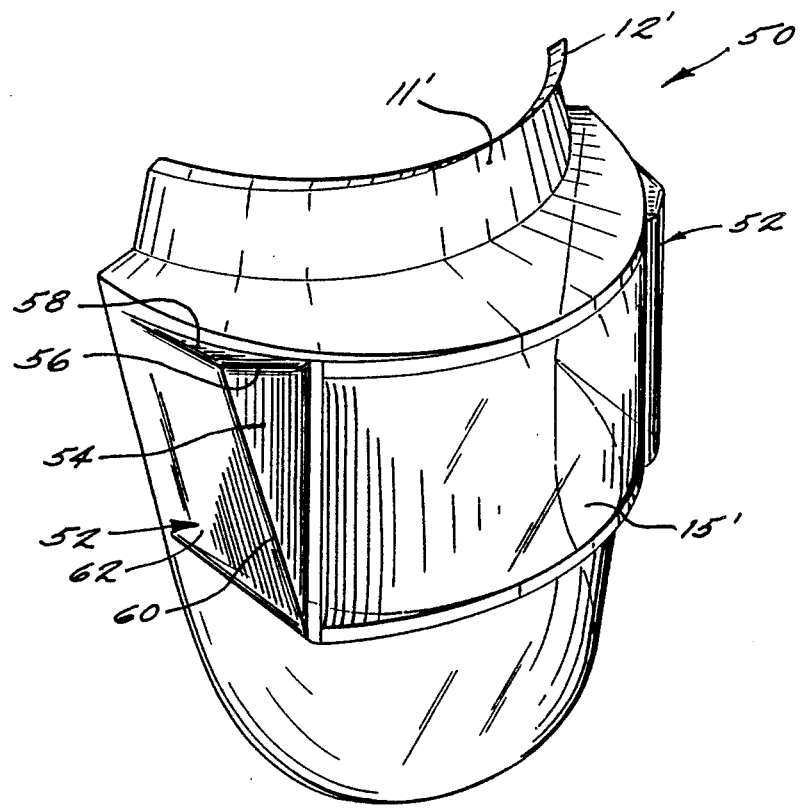
FIG. 10 is a front perspective view of another embodiment of a faceshield in accordance with the present invention.

Turning now to FIG. 10, a preferred embodiment of a disposable faceshield in accordance with the present invention is shown at 50. Faceshield 50 is similar to faceshield 10 of FIGS. 2–5 so that corresponding structural features have been identified in the same manner with the addition of a prime. An important structural distinction between faceshield 50 of FIG. 10 and faceshield 10 of FIGS. 2–5 is the presence of opposed side extensions 52 which extend outwardly from opposed side surfaces of the faceshield adjacent upper viewing portion 15'. Each side extension 52 comprises a triangularly shaped front panel 54 joined along its upper edge 56 to another triangularly shaped top panel 58; and joined along its outer side edge 60 to a substantially parrallelogram shaped panel 62.

Turning to FIG. 18, side extensions 52 are formed during vacuum molding by an appropriately shaped land 64 in the mold 66. A plug 68 applies pressure against the faceshield and land 64 to form an airtight seal so that a vacuum may be drawn through one or more channels 70 in pocket 72. As opposed to the method of molding depicted in FIGS. 6–8, it has now been found advantageous to apply a vacuum to pocket 72 which permits careful control of the optical bubble size and shape.

Figure 11:
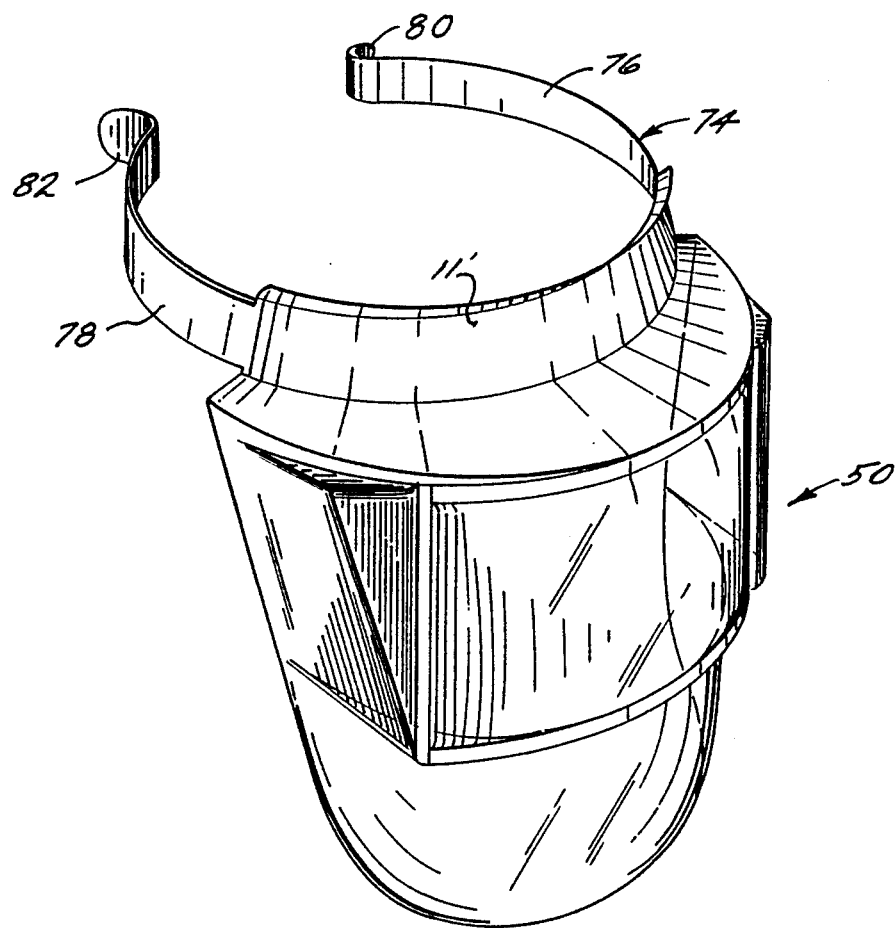
FIG. 11 is a front perspective view of a faceshield with disposable head attachment in accordance with the present invention.
Figure 12:
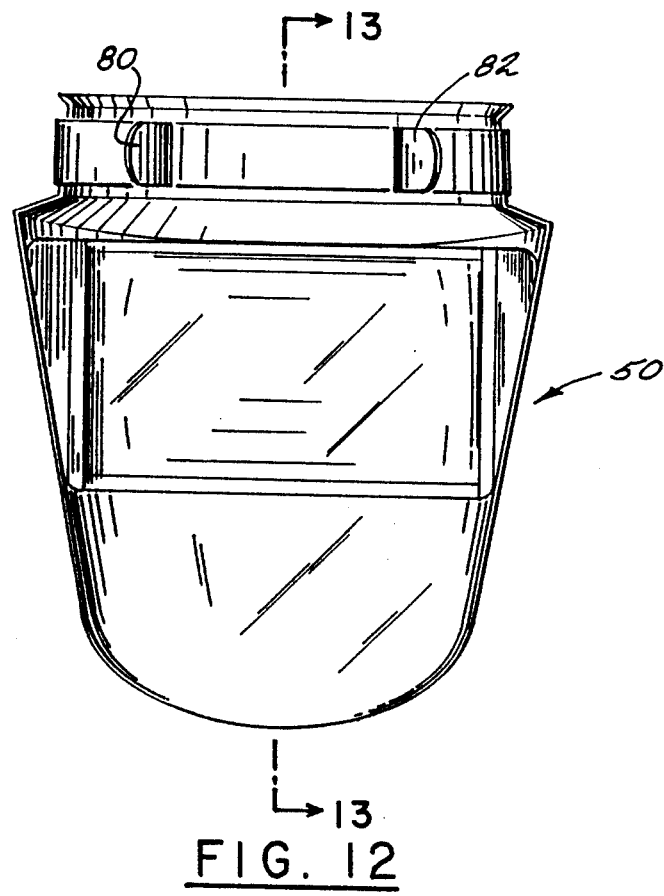
FIG. 12 is a rear elevation view of the faceshield of FIG. 11.
Figure 13:
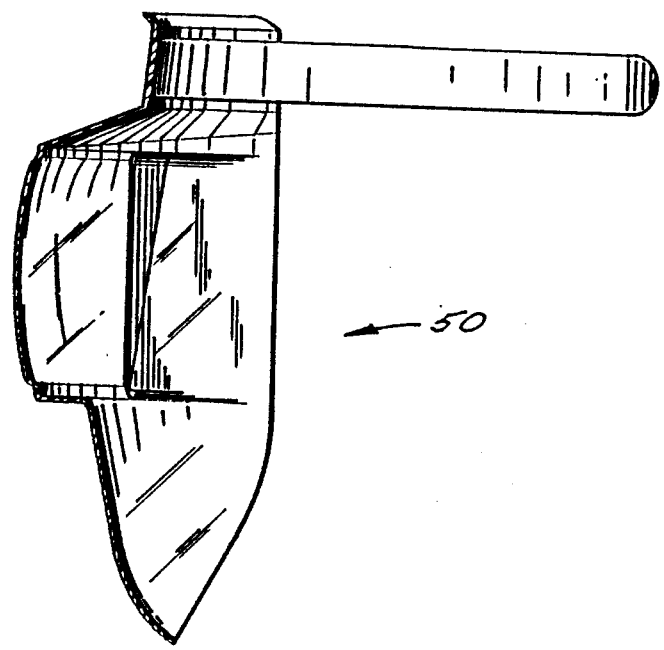
FIG. 13 is a cross sectional elevation view along the line 13—13 of FIG. 12.

Referring now to FIGS. 11–13, faceshield 50 of FIG. 10 is depicted in conjunction with a non-reusable headband 74. Headband 74 is comprised of a resilient material which is preferably plastic such as polyester, polyesterpropionate or polycarbonate. Headband 74 includes a pair of bands 76,78 which may be part of a continuous semi-circular piece or may be discrete members. In any event, headband 74 is attached to brow section 11' by any suitable method including ultrasonic bonding techniques, high frequency RF bonding techniques or by use of a suitable adhesive. Still another method of attaching headband 74 is to mold (e.g. injection mold) the headband directly to the faceshield 50. In this latter case, the previously vacuum formed faceshield would be loaded into a suitable mold; and the resilient members 76, 78 would be molded directly to the faceshield. Headband members 76 and 78 terminate at respective reverse curve sections 80 and 82 which allow easier positioning on the head.

It will be appreciated that the headband 74 of FIGS. 11–13 will allow the faceshield to be easily put on and taken off without the use of elastic bands (FIG. 1) or similar head gear thus allowing for one-handed head attachment. This is particularly advantageous when the faceshield is to be worn in conjunction with other headpieces such as nurse's caps. Thus, the resilient members 76, 78 would simply be pushed onto the wearer's head without the need to remove a previously placed headpiece (e.g. nurse's cap).

Turning now to FIGS. 14–17, still another embodiment of head attaching means for use in conjunction with the one-piece faceshield of the present invention is shown. In this embodiment, the headgear is a reusable unit 84 which is similar in appearance to a known sun visor. Headgear 84 comprises a curved circular member 86 terminating at opposed side members 88 and 90. Side members 88 and 90 terminate at opposed flared pieces 92 and 94 which are similar in appearance and function to members 80 and 82 in FIG. 11. A flanged arcuate section 96 extends outwardly of circular member 86 and has a shape corresponding to the shape of flared surface or skirt 30' of faceshield 50'.

Visor unit 84 includes suitable attachment means for connecting and disconnecting to disposable faceshields. Preferably, circular member 86 includes a plurality (in this case three) of studs or snap shaped protrusions 98 along the exterior thereof. Protrusions 98 could be either attached as a secondary operation or are preferably molded integrally with the visor 84. Faceshield 50' would have locating holes 100 placed along brow portion 11' which would correspond to protrusions 98; and which would be adapted to spread open, pass over studs 98 and be held firmly in place (see FIG. 15). This could be accomplished by providing four small slits 102 equally spaced about holes 100. Of course, any other suitable attachment means between visor 84 and faceshield 50 could be used. For example, the faceshield could be attached to the visor by the use of molded or discrete clips. Such clips could be attached either to the visor or the faceshield. The faceshield could further be attached to visor 84 by the use of double faced adhesive tape, hook and loop type fastening systems or other similar methods.

The reusable headgear of visor 84 has many features and advantages relative to either the elastic band 14 of FIG. 1 or the headgear 74 of FIG. 11. The visor 84 may be inexpensively manufactured (e.g molded) from a suitable plastic and be used over and over again with new faceshields. This reusability will offer a more cost effective headgear relative to the disposable headgear of FIG. 11. In addition, the cost of the disposable faceshield will be lowered relative to the faceshield of FIG. 1 since the elastic strap or band increases the cost of the final product due to labor and materials to cut and attach the elastic strap to the product.

Still another feature of the headgear 84 of FIGS. 14–17 is that flange portion 96 will also offer shielding from overhead light (such as in an operating room) in addition to its function as a support for surface 30'.

Figure 2:
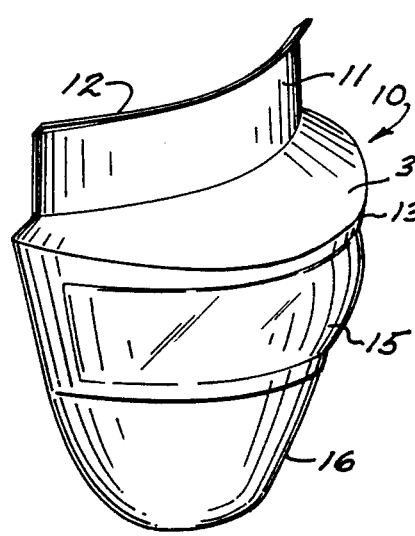
FIG. 2 is a perspective view of a preferred faceshield of the present invention with a bubble-shaped viewing area and a breath-deflecting section.
Figure 14:
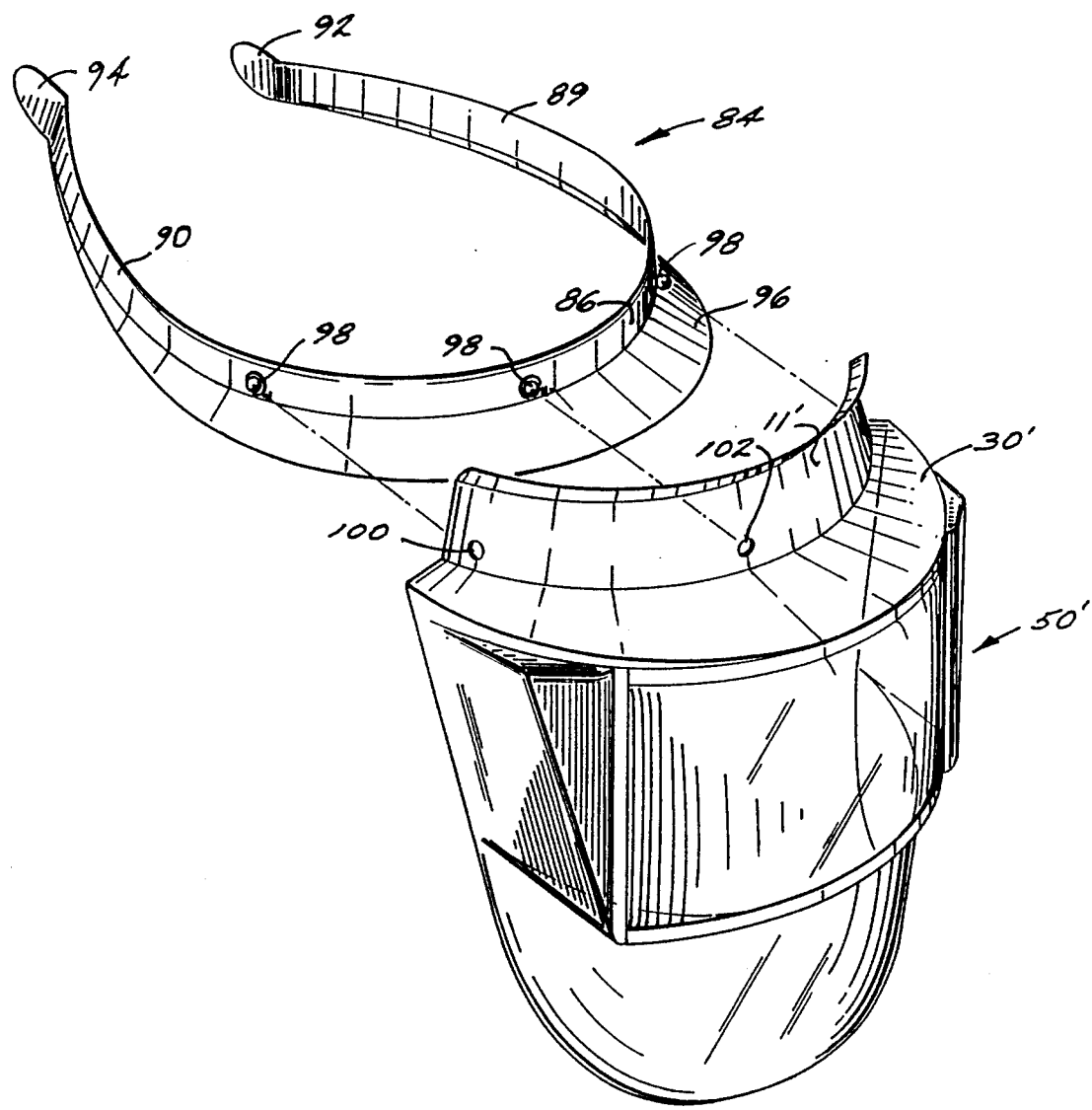
FIG. 14 is an exploded front perspective view of a faceshield with reusable head attachment in accordance with the present invention.
Figure 15:
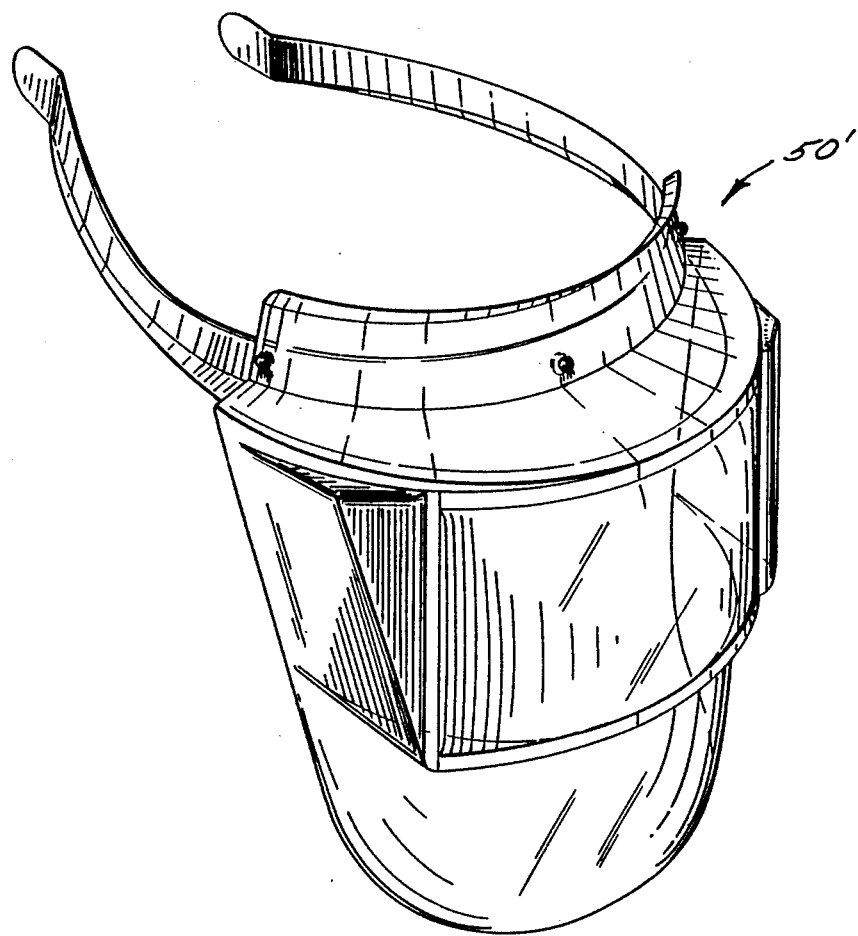
FIG. 15 is a front perspective view of the faceshield of FIG. 14.
Figure 16:
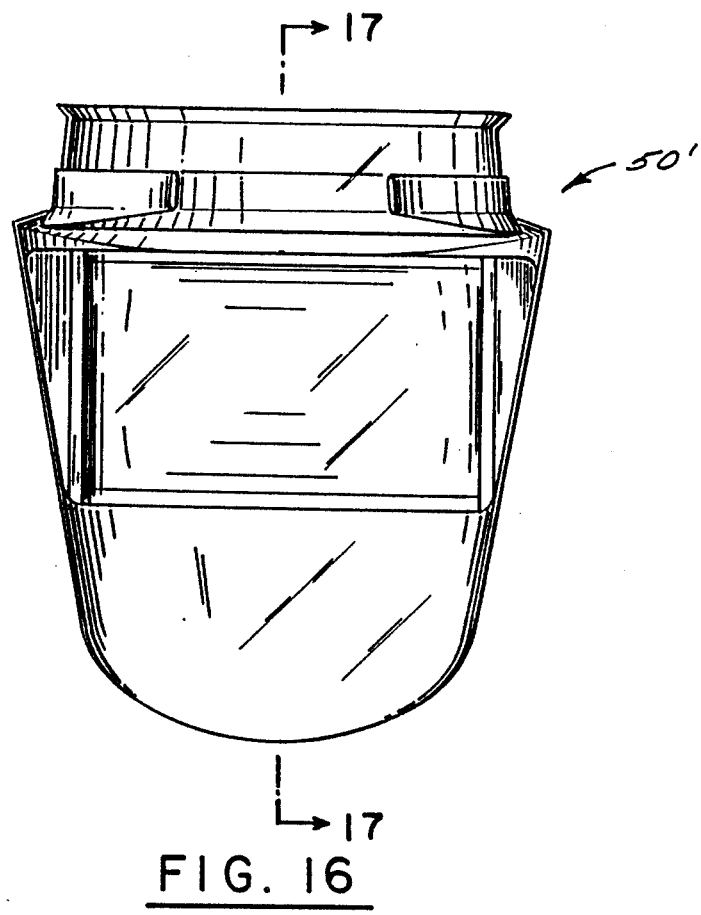
FIG. 16 is a rear elevation view of the faceshield of FIG. 14.
Figure 17:
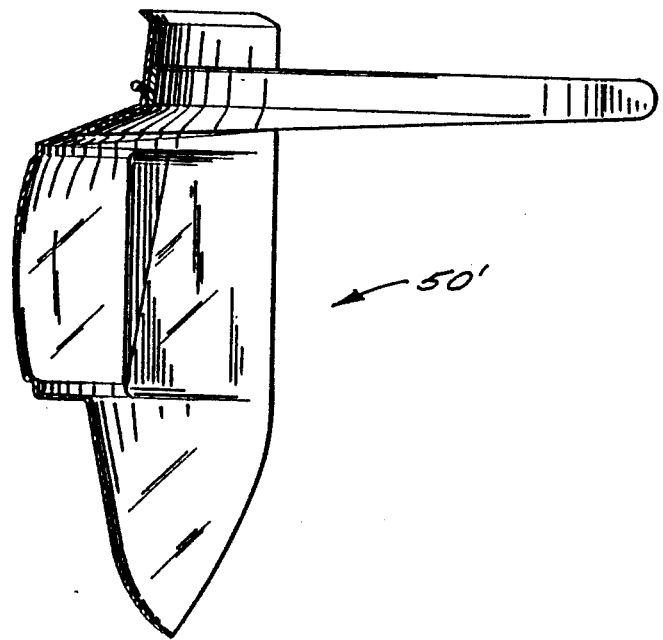
FIG. 17 is a cross sectional elevation view along the line 17—17 of FIG. 16.

It will be appreciated that while the headgear 74 of FIG. 11 and the headgear 84 of FIG. 14 have been shown in conjunction with the faceshield 50 of FIG. 10, headgear designs 74 or 84 may equally be used with any of the other faceshield designs depicted in FIGS. 1, 2 or 9 (goggles).

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method of making a protective shield with an optically clear viewing portion, the viewing portion including a pair of opposed sides which comprises the steps of:

providing a forming mandrel having lands for forming a pair of extensions and a pocket in the area of the viewing portion, wherein said pair of extensions extend outwardly along each opposed side of said viewing portion;

applying a vacuum through holes extending through the lands;

conforming said pair of extensions to the lands; and maintaining said viewing portion of said protective shield out of contact with said forming mandrel to define an optically clear viewing portion.

2. The method of claim 1 wherein said forming mandrel includes and including the step of:

allowing said thermoplastic film to sag partially into said pocket without touching any part of the pocket to form said viewing portion.

3. The method of claim 2 wherein said pocket is free of vacuum holes.

4. The method of claim 2 wherein said pocket includes at least one vacuum hole.

5. The method of claim 1 wherein said viewing portion is bubble shaped.

6. The method of claim 1 wherein:

said extensions have a triangular cross-section.

7. The method of claim 1 wherein said step of conforming said extensions comprise:

forming a triangularly shaped front panel;

forming a triangularly shaped top panel adjacent a first edge of said front panel; and forming a rectangularly shaped rear panel adjacent a second edge of said front panel.

8. The method of claim 7 wherein:

said rear panel has the shape of a parallelagram.

9. The method of claim 1 including the step of:

placing a plug against said thermoplastic film and applying pressure against said thermoplastic film and said land to form a fluid tight seal.

10. The method of claim 9 including the step of:

applying a vacuum to said pocket.

* * * * *